US00PP26059P3

(12) United States Plant Patent
Pierron-Darbonne

(10) Patent No.: US PP26,059 P3
(45) Date of Patent: Nov. 10, 2015

(54) STRAWBERRY PLANT NAMED 'AMANDINE'

(50) Latin Name: ***Fragaria×ananassa* Duch.**
Varietal Denomination: Amandine

(71) Applicant: Darbonne Pepiniere, SAS, Le Barp (FR)

(72) Inventor: Alexandre Pierron-Darbonne, Pamplona (ES)

(73) Assignee: DARBONNE PEPINIERE, SAS (FR)

( * ) Notice: Subject to any disclaimer, the term of this patent is extended or adjusted under 35 U.S.C. 154(b) by 160 days.

(21) Appl. No.: 13/986,460

(22) Filed: May 6, 2013

(65) Prior Publication Data

US 2014/0331369 P1 Nov. 6, 2014

(30) Foreign Application Priority Data

May 10, 2012 (QZ) ..... 2012/1035

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para

(74) *Attorney, Agent, or Firm* — Knobbe, Martens, Olson & Bear, LLP

(57) ABSTRACT

A new and distinct strawberry variety, *Fragaria ananassa*, cv. 'Amandine' is characterized by a position of the inflorescence that appears above the foliage, same size of calyx relative to corolla, and abundant production of dark red colored, cordiform shaped, and medium firm fruit, which appears to be characterized by large fruit size, and early time of ripening (50% of plants with ripe fruits).

9 Drawing Sheets

Latin name of the genus and species claimed: *Fragaria× ananassa* Duch.

Variety denomination: 'Amandine'.

BACKGROUND AND SUMMARY OF THE INVENTION

The present invention relates to a new and distinct strawberry variety. The varietal denomination of the new variety is 'Amandine'. The new variety was designated by the breeder as 'Amadine DA 47'. The new variety of strawberry was created in a breeding program by crossing two parents in 2005 in Le Barp, France; in particular, by crossing as seed parent an undistributed strawberry parent designated '88.09.06' (unpatented) and as pollen parent an strawberry parent designated 'Mara des Bois' (U.S. Plant Pat. No. 8,517). Seed parent is a selection from breeder's program and has not been commercialized.

The resulting seedling of the new variety was grown and asexually propagated by runners in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Gironde, France, where the observations were made, is between about May, 15 and October, 15 of each year, with a maximum production at about beginning July. 'Amandine' is a fully remontant (non flowering runners) variety that benefits from induction to flowering by very low chilling, usually a few hours are sufficient, preferably at temperatures of 7° C. or less.

Among the characteristics which appear to distinguish the new variety from other varieties are a combination of traits which include: inflorescence that appears above relative to the foliage, same size of calyx relative to corolla and abundant production of orange red colored, cordiform shaped, and medium firm fruit, large fruit size, and early time of ripening (50% of plants with ripe fruits).

The new variety 'Amandine' is distinguished there from its Seed parent '88.09.06' (unpatented) in that the new variety is more vigorous and the production of commercial quality fruit of seed parent '88.09.06' (unpatented) is about 478 g/plant compared to that of the new variety 'Amandine' of about 513 g/plant. The Seed parent '88.09.06' (unpatented) shows a red fruit color about Medium Orange-Red 34C to Medium Orange-Red 34B less intense than in the new variety 'Amandine' about Medium Red 45B to Medium Red 45A.

The new variety 'Amandine' is distinguished there from its pollen parent 'Mara des Bois' (U.S. Plant Pat. No. 8,517) in that the new variety has a larger fruit size of approximate 13 to 15 g/fruit compared to approximate 10 to 12 g/fruit of the pollen parent. The Pollen parent 'Mara des Bois' (U.S. Plant Pat. No. 8,517) shows a more intense red fruit color about Medium Red 46B to Dark Red 46A compared to that of the new variety 'Amandine' of about Dark Red 45B to Dark Red 45A.

The new variety 'Amandine' is closest to the variety 'Charlotte' (unpatented) but is distinguished therefrom by having a flat globose habit compared to flat in 'Charlotte' (unpatented). The shape of base of terminal leaflet in 'Charlotte' (unpatented) is obtuse compared to acute in 'Amandine', and the new variety 'Amandine' has a smaller number of stolons than 'Charlotte' (unpatented). Meanwhile, the position relative to the foliage of the inflorescence in 'Charlotte' (unpatented) is level with, while it is above in 'Amandine'. the fruit color of 'Charlotte' (unpatented) is about Medium Red 46C to Medium Red 46B, whereas in 'Amandine' it is a red fruit color Medium Red 45B to Dark Red 45A, while the color of flesh in fruits of 'Charlotte' (unpatented) is about Medium Red 40C to Medium Red 40D, whereas the color of flesh in fruits of 'Amandine' is about Medium Orange-Red 31B to Medium Orange-Red 32B. The Predominant shape of fruit in 'Charlotte' (unpatented) is conical, than the predominant shape of fruit in 'Amandine' is cordiform.

The differences in the position of the inflorescence relative to foliage in 'Amandine' and 'Charlotte' (unpatented) are shown in FIG. 1 and FIG. 5 respectively. The differences in the shape of the base of the terminal leaflet of 'Amandine' and 'Charlotte' (unpatented) are shown in FIG. 4 and FIG. 5 respectively. The differences in the shape and color of the fruit of 'Amandine' and 'Charlotte' (unpatented) are shown in FIG. 7 and FIG. 9 respectively.

BRIEF DESCRIPTION OF PHOTOGRAPHS

The accompanying photographs show typical specimens of the new variety, designated 'Amandine' in the illustrations, including fruit, foliage and flower, in color as nearly true as it is reasonably possible to make in color illustrations of this character.

The plants depicted in the photographs were planted Apr. 12, 2011 in Gironde, France, about 0.70° W., 44.60° N., 165 feet elevation.

Photographs were taken June-July, 2011 (about Jun. 25 and Jul. 10, 2011): minimum temperate about 10 to 12° Centigrade, maximum temperate about 24 to 26° Centigrade.

FIG. 5 shows the leaves and the terminal leaflet of the strawberry variety 'Charlotte' (unpatented). In it we can see that the shape of the base of terminal leaflet is obtuse and the position, relative to the foliage is level with.

DESCRIPTION OF THE NEW VARIETY

Figure 1:
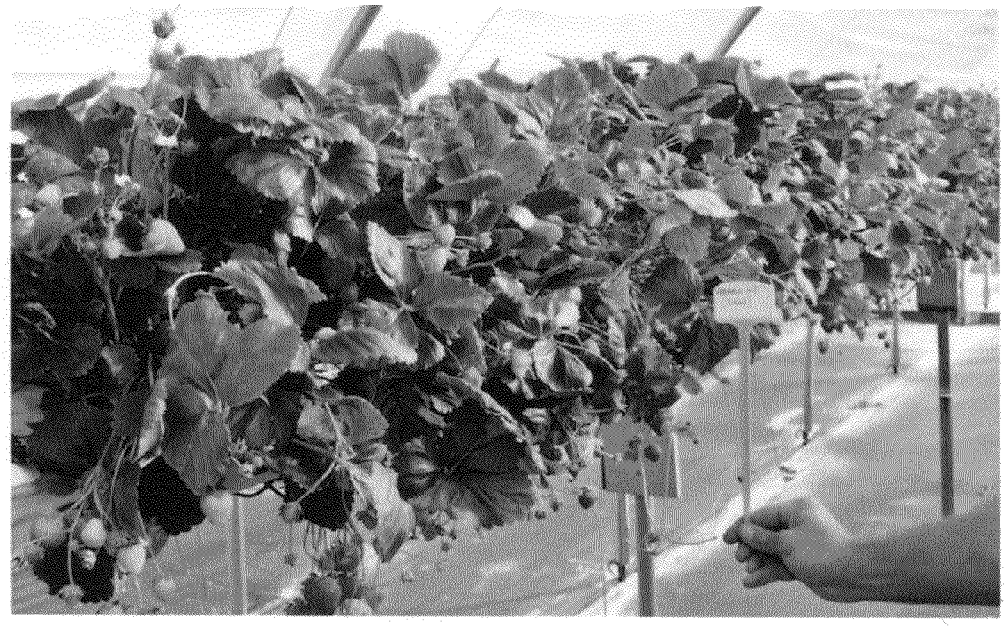
FIG. 1 shows several plants of the new variety 'Amandine' which exhibit a plant medium dense and the position of the inflorescence relative to foliage is above.
Figure 2:
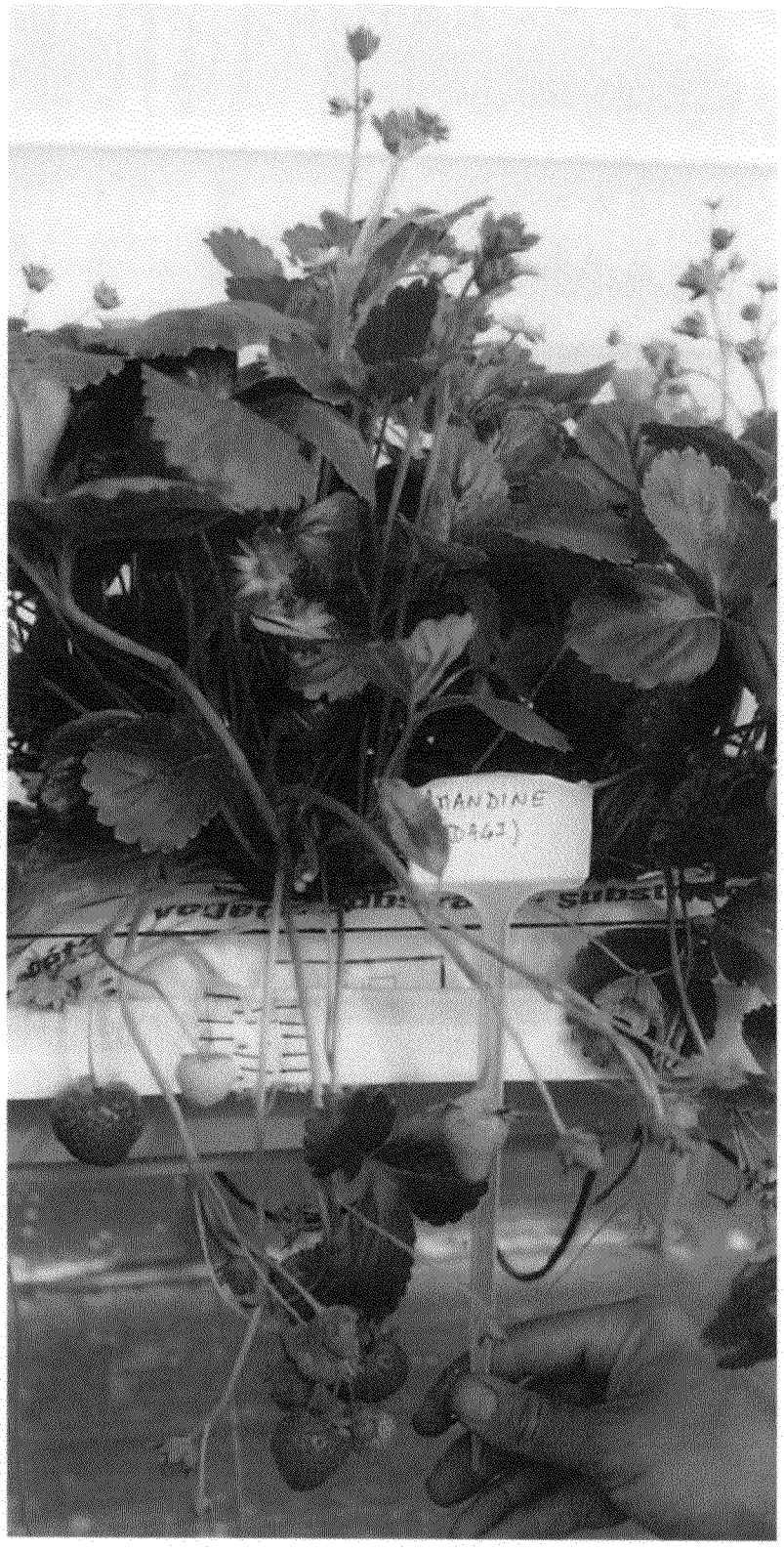
FIG. 2 shows several plants of the new variety 'Amandine' with several red colored and cordiform shape fruits.
Figure 3:
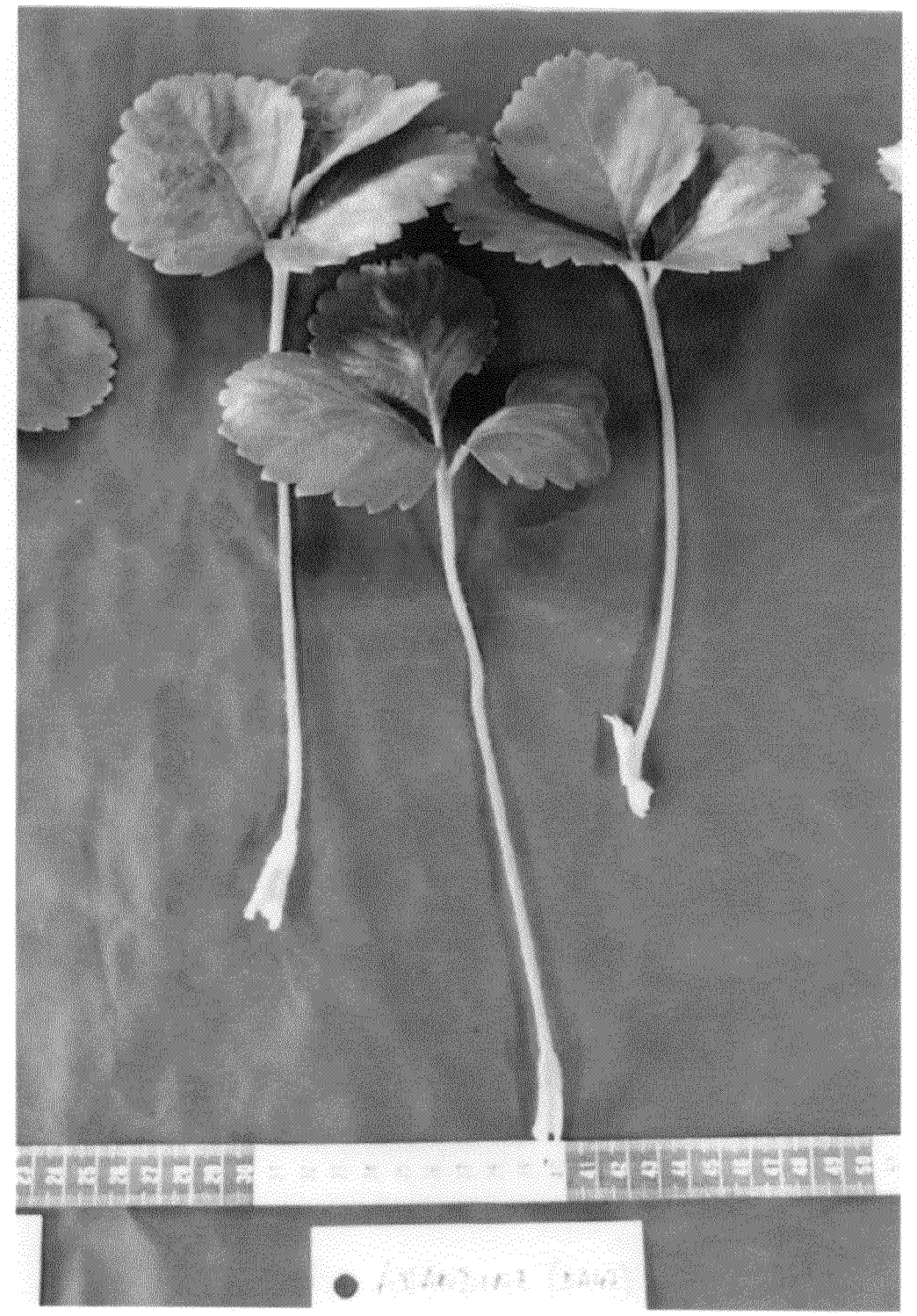
FIG. 3 shows the upperside of a complete leave of the new variety 'Amandine.'. In it we can see that the leaf color of upper side of the new variety 'Amandine' is about Medium Green 138C to Medium Green 138B.
Figure 4:
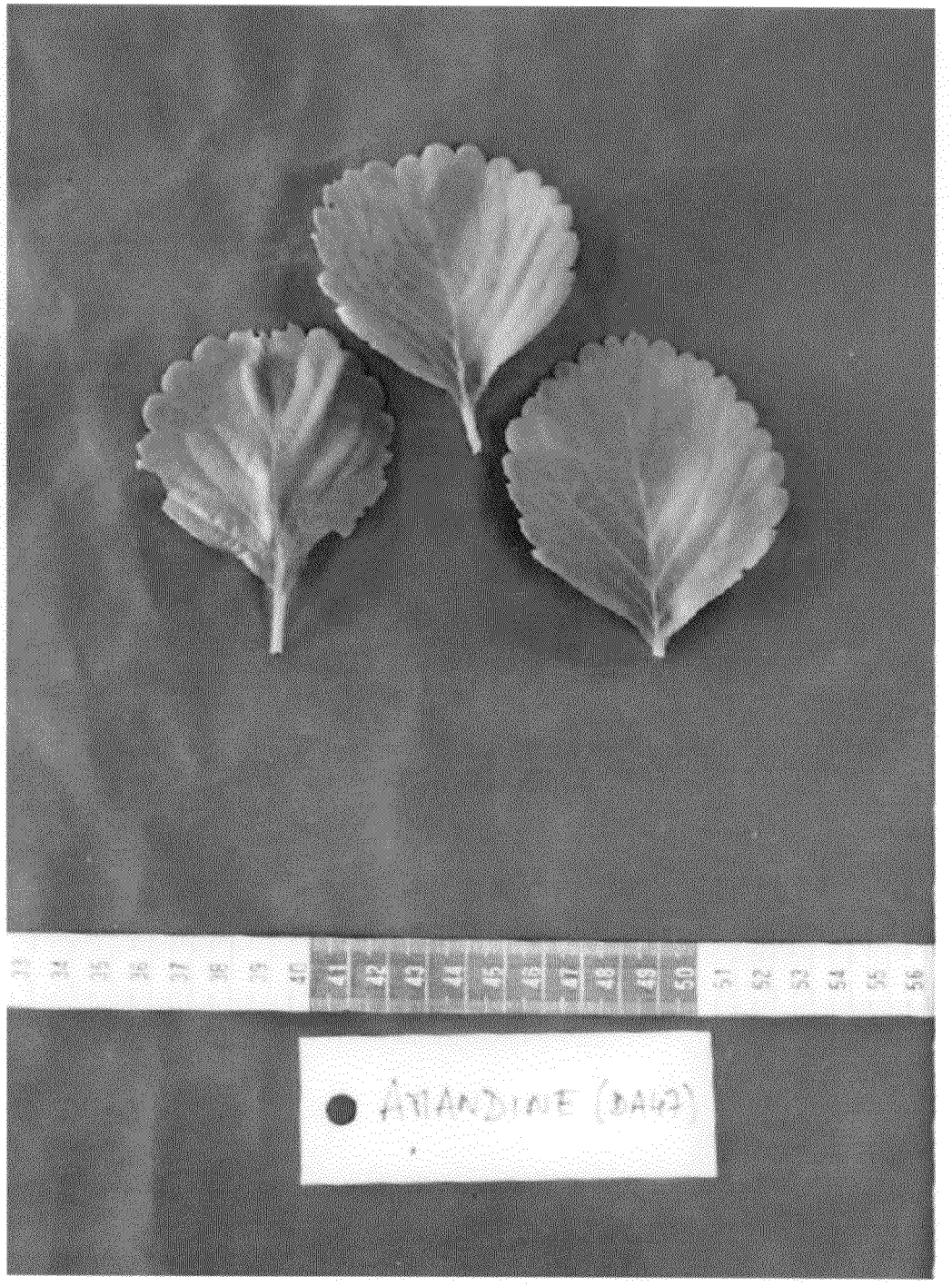
FIG. 4 shows the upperside of terminal leaflet of the new variety 'Amandine'. In its we can see that the leaf color of upper side of the new variety 'Amandine' is about Medium Green 138C to Medium Green 138B and the shape of the terminal leaflet is acute.
Figure 5:
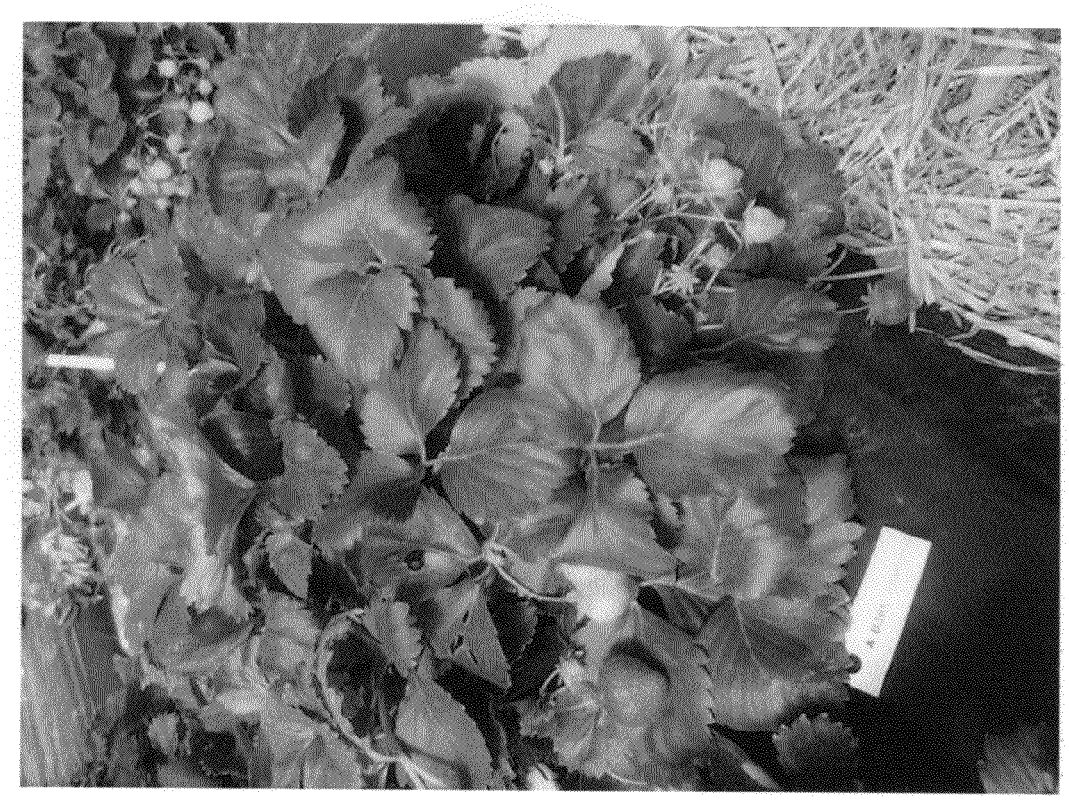
Figure 6:
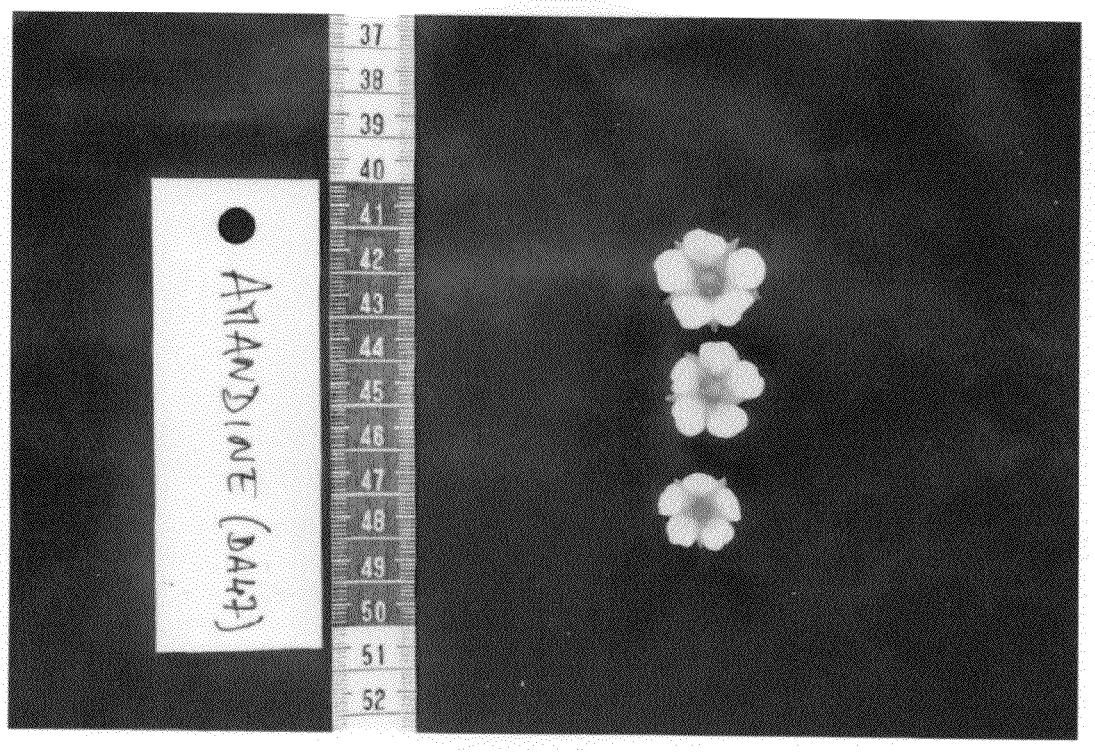
FIG. 6 shows the flower of the new variety 'Amandine'.
Figure 7:
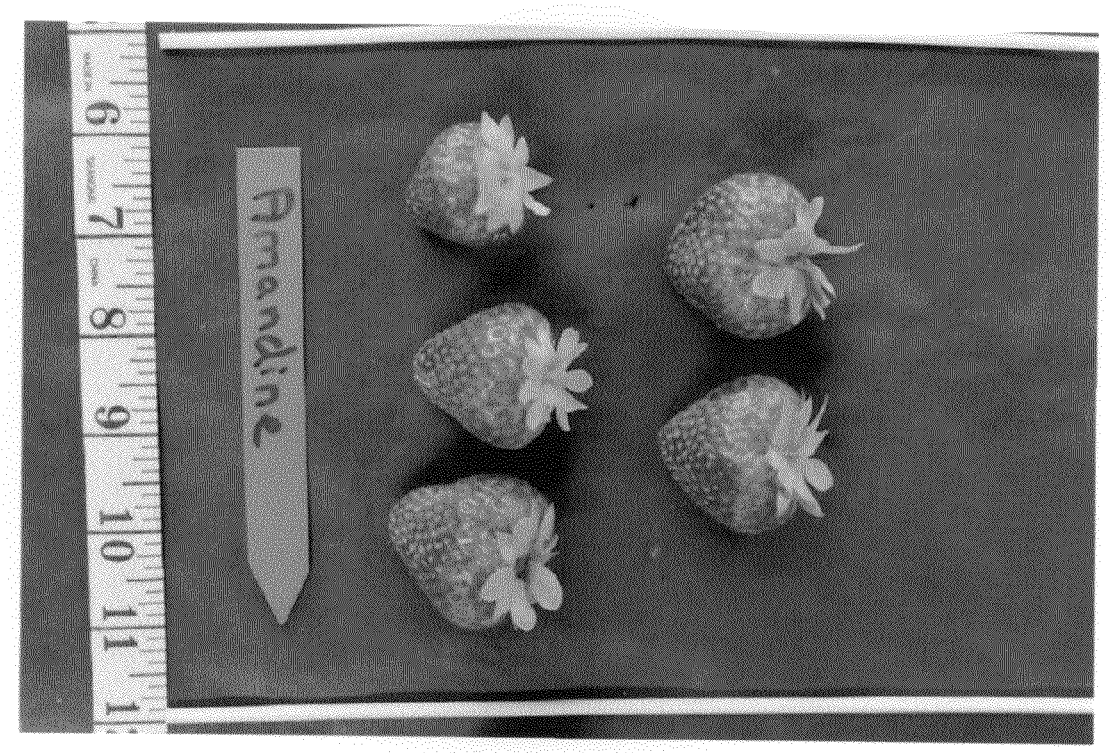
FIG. 7 shows typical whole fruit of the new variety 'Amandine' illustrating the typical cordiform shape fruit and red fruit color about Dark Red 45B to Dark Red 45A.
Figure 8:
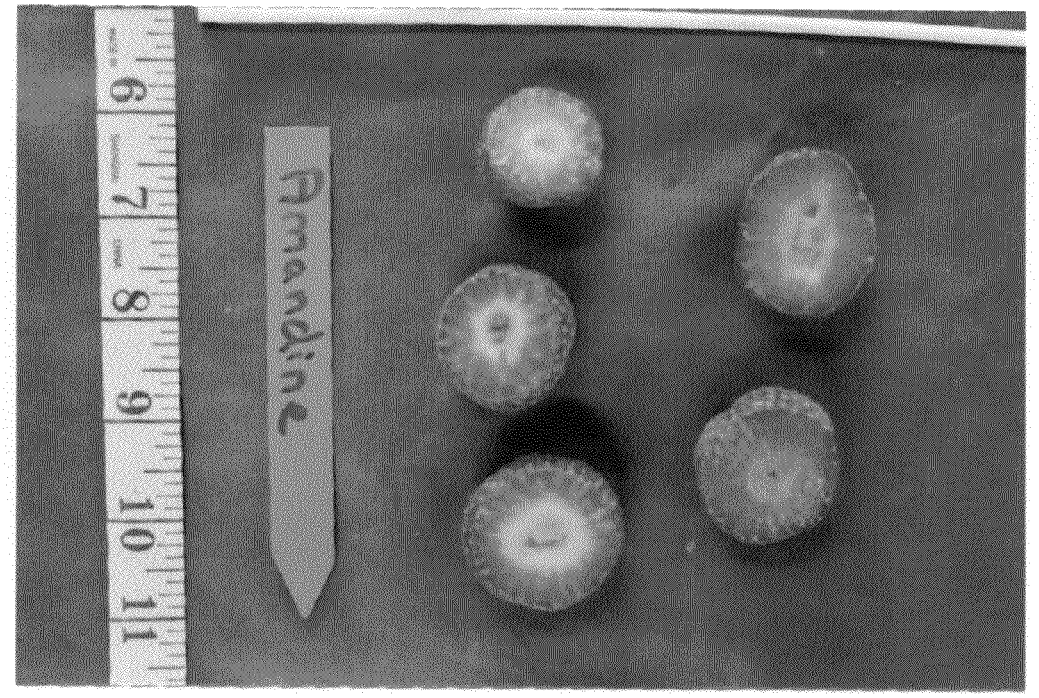
FIG. 8 shows typical sliced section, illustrating the typical flesh coloration about Medium Orange-Red 31B to Medium Orange-Red 32B, with a weakly expressed hollow center.
Figure 9:
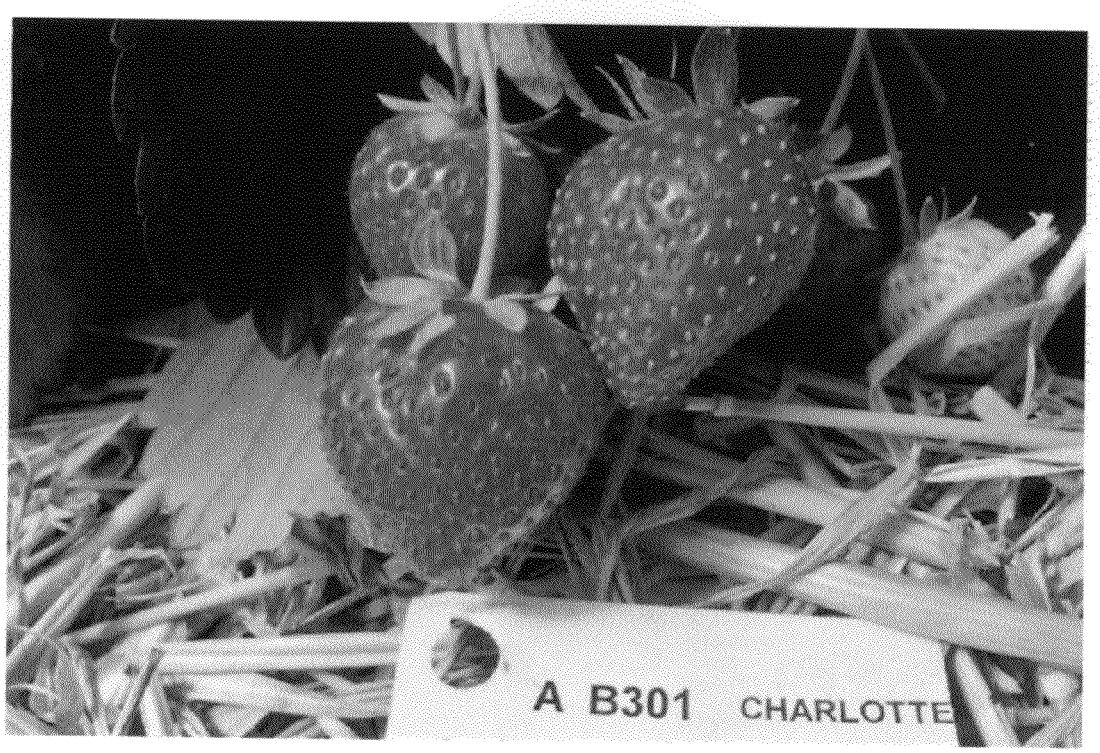
FIG. 9 shows typical whole fruit of the strawberry variety 'Charlotte' (unpatented) illustrating the typical conical shape fruit and red fruit color about Medium Red 46C to Medium Red 46B.

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown "underglass", i.e. under tunnel, in Gironde, France, 0.70° W., 44.6° N., 165 feet elevation on Apr. 12, 2011. After planting, plants are grown in tabletop under 5 meters tunnel covered with plastic. Water and fertilizer are applied through drip irrigation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface ondulation inherent to leaves and is generally a constant characteristic.

'Amandine' is a long day variety that needs an induction to flowering by very low chilling, such as occurs at a high elevation nursery. Usually a short time is sufficient. 'Amandine' is self-fertile. It produces large quantity of pollen throughout the seasons and pollination is generally good as there are very few malformed fruit.

Measurements and descriptions were taken at two different times during the year, i.e. August and October with a sample size of 50 plants per repetition. After planting, plants are grown in tabletop under 5 meters tunnel covered with plastic. Water and fertilizer are applied through drip irrigation. 10% of the flowering occurred on May 10, 2011, the first mature fruits occurred on Jun. 8, 2011 and full maturity (15-20 h/plant) occurred on Jun. 20, 2011.

Table 1 shows the Accumulated Production of Commercial Quality Fruit (g/plant) of the new variety 'Amandine' when compared to its pollen parent and closest varieties 'Charlotte' and 'Evie2' during the months of August and October.

TABLE 1

| Variety | August 9 | October 17 |
|---|---|---|
| AMANDINE | 250 | 513 |
| MARA DES BOIS | 225 | 562 |
| EVIE2 | 242 | 699 |
| CHARLOTTE | 220 | 521 |

Table 2 shows the Total Yield to October 17 and fruit weight average of the new variety 'Amandine' when compared to its pollen parent and closest varieties 'Charlotte' and 'Evie2' during the months of August and October.

TABLE 2

| Variety | 1st + 2nd Quality Fruit | Total | Weight (g/fruit) |
|---|---|---|---|
| AMANDINE | 319 + 194 | 513 | 15 |
| MARA DES BOIS | 261 + 301 | 562 | 10 |
| EVIE2 | 520 + 179 | 699 | 16 |
| CHARLOTTE | 339 + 182 | 521 | 12 |

Table 3 shows the Production Total, to October 17, of First Quality Fruit ($1^{st}$ quality) and Second Quality Fruit ($2^{nd}$ quality) in g/plant, of the new variety 'Amandine' when compared to its pollen parent and closest varieties 'Charlotte' and 'Evie2'.

TABLE 3

| Variety | $1^{st}$ quality | $2^{nd}$ quality | TOTAL ($1^{st}$ quality + $2^{nd}$ quality) | % $2^{nd}$ quality |
|---|---|---|---|---|
| AMANDINE | 319 | 194 | 513 | 37.8 |
| MARA DES BOIS | 264 | 301 | 562 | 53.5 |
| EVIE2 | 520 | 179 | 699 | 25.6 |
| CHARLOTTE | 339 | 182 | 521 | 34.9 |

$$\%\ 2^{nd}\ \text{quality} = \frac{2^{nd}\ \text{quality}}{\text{TOTAL}} \times 100$$

Table 4 shows the Weight (g/Fruit) at two dates: August 9 and October 17 of the new variety 'Amandine' when compared to its pollen parent and closest varieties 'Charlotte' and 'Evie2'.

TABLE 4

| WEIGHT (g/fruit) | August 9 | October 17 |
|---|---|---|
| AMANDINE | 13 | 15 |
| MARA DES BOIS | 12 | 10 |
| EVIE2 | 14 | 16 |
| CHARLOTTE | 14 | 12 |

WEIGHT is shown as the average weight per fruit in First Quality Fruits.

Table 4 shows a comparison of the fruit analysis between the new variety 'Amandine', its pollen parent and closest varieties 'Evie2'.

TABLE 5

| | EVIE 2 | AMANDINE (DA 47) | MARA DES BOIS |
|---|---|---|---|
| Firmness (Kg) | 0.40 | 0.60 | 0.40 |
| Humidity & Volatile Matter (%) | 91.40 | 91.90 | 92.10 |
| Dry Matter (%) | 8.60 | 8.10 | 7.90 |
| PH (to 20°) | 3.60 | 3.90 | 3.50 |
| Acidity as Anhydride Citric (%) | 0.46 | 0.47 | 0.45 |
| Soluble Solids (° Brix) | 5.00 | 7.00 | 6.20 |
| Maturity Index | 10.90 | 14.90 | 13.80 |
| Content in Ascorbic Acid (mg/Kg) | 14.30 | 9.80 | 10.60 |
| Dominant Tonality(nm) | 500 | 500 | 500 |
| Luminosity: Transmitance to 460 nm | 63.80 | 25.60 | 42.10 |

* obtained by the penetrometer ROZE Mod. Arbelette, with a 50 $mm^2$ section head Dry Matter: It is the weight of the residual left from the trituration of the fruit after the drying process at a temperature of 103° C.±2° C. until reaching constant weight.

$$(\%)\ \text{Dry Matter} = \frac{\text{Weigth Dry Matter}}{\text{Weigth Fresh Matter}} \times 100$$

Humidity & Volatile Matter: Represents the content in volatile matters and water of the fruits.

(%) Humidity & Volatile Matter=100−% Dry Matter

Maturity Index: Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

Plant:

*Habit.*—Falt globose.
*Density.*—Medium.
*Vigor.*—Medium.
*Height.*—Long (About 30 cm).
*Width.*—Long (About 30 cm).
*Growth habit.*—Semi-upright.

Leaf:

*Size.*—Medium.
*Upperside.*—About Medium Green 138C to Medium Green 138B.
*Underside.*—About Light Green 139D to Medium Green138D).
*Length.*—About 7 cm.
*Width.*—About 13 cm.
*Cross section.*—Slightly concave.
*Leaf surface ondulation or blistering.*—Medium.
*Number of leaflets.*—Three only.
*Glossiness.*—Medium.
*Variegation.*—Absent.

Leaf stem characteristics:

*Color.*—About Light Yellow-Green 144D to Medium Yellow-Green 145B.
*Position of hairs.*—Sligthly outwards.
*Length.*—About 10 to 12 cm.

Terminal leaflet:

*Length/width ratio.*—As long as broad.
*Length.*—Medium (About 7 to 8 cm).
*Width.*—Medium (About 7 to 8 cm).
*Shape of base.*—Obtuse.
*Shape of teeth.*—Crenate.
*Margin.*—Crenate.
*Shape in cross section.*—Concave.

Petiole:

*Position of hairs.*—Sligthly outwards.
*Length.*—MEDIUM, about 10 to 12 cm.

Stipule:

*Anthocyanin coloration.*—Medium, about Light Yellow-Green 145D to Light Yellow-Green 145C.

Stolons:

*Number.*—Few, about 3 to 5.
*Antocyanin coloration.*—Medium.
*Thickness.*—Thin, about 2 to 3 mm.
*Pubescence.*—Medium.
*Length.*—Medium (about 35 to 40 cm).
*Color.*—About Light Yellow-Green144D to Medium Yellow-Green 145B.

Inflorescence:

*Position relative to foliage.*—Above.
*Number of flowers.*—Medium to many, about 5 to 7.

Flower:
*Size.*—Medium.
*Size of calyx relative to corolla.*—Medium.
*Arrangement of petals.*—Touching.

Flower characteristics:
*Diameter primary flowers.*—Medium (About 2.7-3.0 cm).
*Diameter secondary flowers.*—Short (About 1.9-2.2 cm).
*Number of petals.*—Normally about 5.
*Fragance.*—No significant fragance.
*Time from bloom to mature fruit* (*Huelva, Spain*).—About 35 to 40 days.
*Stamens.*—Present, numerous with pollen present, fertile and abundant.
*Length.*—Approximatelly 3-3.5 mm.
*Stamens color.*—About White 155D to White 155C.
*Anthers.*—Generally average in size.
*Anthers color.*—About Medium Yellow 12B to Medium Yellow 13B, and darkening with advanced maturity.
*Pollen.*—Fertile and abundant.
*Pollen color.*—About Dark Yellow 15B to Medium Yellow 14A.
*Pistils.*—Numerous, generally average in size.
*Pistils color.*—About Medium Yellow group 13B to Medium Yellow 13A.

Petal:
*Length/width ratio.*—As long as broad.
*Length.*—Medium (Approximately 8 to 9 mm).
*Width.*—Medium (Approximately 8 to 9 mm).
*Shape.*—Rounded.
*Color.*—About White 155D to White 155D.

Fruiting truss:
*Attitude.*—Semi-erect.

Fruit:
*Ratio of length/maximum width.*—As long as broad.
*Color.*—About Dark Red 45B to Dark Red 45A.
*Peduncle length of inflorescence stem.*—Primary fruit about 28 to 30 cm, secondary fruit about 25 to 27 cm.
*Peduncle color.*—About Light Yellow-Green 145C to Medium Yellow-Green 145B.
*Size.*—Large.
*Shape.*—Cordate.

Primary fruit:
*Length.*—Long (About 4.0 to 4.5 cm).
*Width.*—Medium (About 3.5 to 4.0 cm).

Secondary fruit:
*Length.*—Medium (About 3.0 to 3.5 cm).
*Width.*—Short (About 3.0 to 3.5 cm).
*Size.*—Large.
*Predominant shape.*—Cordiform.
*Difference in shapes between primary and secondary fruits.*—Slight.
*Band without achenes.*—Very broad.
*Color of achenes.*—About Light Orange-Red 31C to Medium Orange-Red 32C.
*Position of achenes.*—Level with surface.
*Unevenness of surface.*—Absent or very weak.
*Evenness of color.*—Uneven.
*Glossiness.*—Medium.
*Evenness of surface.*—Even or very slightly uneven.
*Insertion of achenes.*—Level with surface.
*Insertion of calyx.*—Level with fruit.
*Pose of the calyx segments.*—Spreading.
*Diameter of calyx in relation to diameter of fruit.*—Slightly smaller.
*Calyx.*—Presents 8 to 9 sepals with lanceolate shape in addition 3 to 4 sepals smaller sepals with less shape.
*Color upperside of sepals.*—About Light Yellow-Green 145C to Medium Yellow-Green 145B.
*Color underside of sepals.*—About Light Yellow-Green 144D to Medium Yellow-Green 145B.
*Length of sepals.*—Medium (About 7.0 to 9.0 mm).
*Width of sepals.*—Short (About 3.0 to 5.0 mm).
*Adherence of calyx.*—Medium.
*Firmness.*—Medium.
*Color of flesh.*—About Medium Orange-Red 31B to Medium Orange-Red 32B, lightening towards the center.
*Color of core.*—About Light Orange 27C to Light Orange 29C.
*Cavity.*—Medium.
*Distribution of red color of flesh.*—Marginal and central.
*Hollow center.*—Weakly expressed.
*Sweetness.*—Medium. 7.0° Brix.
*Acidity.*—Medium. 0.47% (Acidity as Anhydride Citric).
*Time of flowering* (50% *of plants at first flower*).—Early.
*Time of ripening* (50% *of plants with ripe fruits*).—Early, about Jun. 14, 2011.
*Type of bearing.*—Fully remontant (non flowering runners).
*Chilling.*—About 300 hours.

Disease resistance: No particular sensitivity to any disease or parasite has been observed for 'Amandine'.

Storage qualities: 'Amandine' fruit maintain their quality characteristics when keeping them in a frigo chamber at temperatures of about 2° C. during 48 hours. The fruit's color remains substantially the same.

I claim:

1. A new and distinct strawberry plant of the variety substantially as shown and described.

* * * * *